United States Patent [19]

Tolbert et al.

[11] 4,273,871

[45] Jun. 16, 1981

[54] PRODUCTION OF ANGIOGENIC FACTOR BY CELL CULTURE

[75] Inventors: William R. Tolbert, Manchester; Mary M. Hitt, St. Louis; Joseph Feder, University City, all of Mo.

[73] Assignee: Monsanto Company, St. Louis, Mo.

[21] Appl. No.: 126,810

[22] Filed: Mar. 3, 1980

[51] Int. Cl.$^3$ ............................................... C12P 1/00
[52] U.S. Cl. ...................................... 435/41; 435/240; 435/948
[58] Field of Search ......................... 435/41, 240, 241

[56] References Cited

PUBLICATIONS

Adv. Cancer Res. 19, 331–358 (1974).
Arch Dermatol. 111, 321–327 (1975).
J. Invest. Dermatol, 61, 130–141 (1973).
Microvas. Res. 10, 396–413 (1975).
Proc. Natl. Acad. Sci. USA 75, (2) 841–851 (1978).
Cancer Res. 36, 110–114 (1978).
Kruse et al., Tissue Culture Methods and Applications pp. 593–599 (1973).

Primary Examiner—Alvin E. Tanenholtz
Attorney, Agent, or Firm—Scott J. Meyer; James W. Williams, Jr.

[57] ABSTRACT

Process for the production of human angiogenic factor in vitro comprising growing cells of human foreskin fibroblast cell line on support surface in nutrient culture medium at about 35°–38° C. for a sufficient time to elaborate angiogenic factor and recovering the resulting angiogenic factor from the cells or cell product.

5 Claims, No Drawings

PRODUCTION OF ANGIOGENIC FACTOR BY CELL CULTURE

BACKGROUND OF THE INVENTION

This invention relates to the in vitro production of human angiogenic factor from human foreskin fibroblast cell lines.

Angiogenesis, or the ability to stimulate blood vessel growth, is important to burn and wound healing and certain inflammatory reactions as well as to tumor growth. The substance that is released by tumors and provides vascularization has been named tumor angiogenesis factor (TAF) by Dr. Judah Folkman of the Harvard Medical School. *J. Exptl. Med.* 133, 275–88 (1971); *Ann. Surg.* 175, 409–16 (1972); *Cancer Res.* 34, 2109–13 (1974); and *Advan. Cancer Res.* 19, 331–58 (1974). Provision for the availability of TAF is particularly useful as an aid to the search for ways to inhibit neovascularization. While TAF also finds use in the development of tests such as an angiogenic assay or a diagnositc screening test for neoplasia, for use in patient treatment an angiogenic material derived from normal rather than tumor cells would be much preferred from the standpoint of safety.

Various investigators in the field have reported heretofore that angiogenic activity is either absent or weak in most normal tissue extracts or grafts or cell culture extracts. Thus, in a paper by Folkman on "Tumor Angiogenesis", *Advan. Cancer Res.* 19, 331–58 (1974), only two exceptions were found to the "general rule that normal adult and embryonic tissues do not induce neovascularization." The observed exceptions were that pieces of embryonic and adult mouse kidney induced mild neovascularization when grafted to the chorioallantoic membrane (CAM) of the chick embryo and that salivary gland from the adult mouse also seemed to be able to induce neovascularization on the CAM. In another group from the same research group by Auerback et al., *Int. J. Cancer* 15, 241–5 (1975), it was reported that control or irradiated placental and muscle tissue from rabbits did not cause a vascular response comparable to that obtained with Walker rat carcinosarcoma and other tumors either with or without irradiation. Klogsbrun et al., *Cancer Res.* 36, 110–14 (1976), subsequently reported that TAF was not detected in normal liver and kidney or in density-inhibited BALB/c primary mouse embryo or early passage human skin fibroblasts, but that density-inhibited BALB/c 3T3 and WI 38 human embryonic lung fibroblasts did produce TAF.

Another group of investigators, Wolf and Hubler, *Arch Dermatol* 111, 321–27 (1975), also investigated the elaboration of TAF by various implated tumors. In parallel tests, angiogenesis was found to be conspicuously absent after implantation of control materials and nevoid or normal cutaneous components with the exception of human and hamster epidermis.

Gimbrone and Gullino, *J. Nat. Cancer Inst.* 56 (2), 305–18 (1976), studied the implantation of mouse mammary tissue in rabbit cornea. They found that while neoplastic tissue stimulated blood vessel growth, normal tissue rarely produced any vascular change.

Phillips et al., *Int. J. Cancer* 17, 549–58 (1976) and 23, 82–88 (1979), found that rat liver, normal human kidney and various other normal or foetal tissues failed to induce angiogenesis.

On the other hand, significant angiogenic factor has been found in normal tissue by several investigators. Thus, Wolf et al., *J. Invest. Dermatol.* 61, 130–41 (1973), reported on an epidermal angiogenic factor from separated hamster epidermis and epidermal extracts as an exception to the general finding that normal tissues do not induce neovascularization when implanted onto the hamster cheek pouch.

Huseby et at., *Microvas. Res.* 10, 396–413 (1975), reported on a normal tissue explant system for 1-day old mouse testes that stimulated proliferation of host blood vessels in adult mice.

The corpus luteum was also found to produce a diffusible substance similar to TAF as a blood growth stimulant by Oehme et al., East German Patent 128,368 (1977); and by Gospodarowicz et al., *Proc. Natl. Acad. Sci. USA* 75 (2), 847–851 (1978).

All of the foregoing normal human cells are derived from fresh tissue or primary cultures except the WI 38 cells. Fresh tissue and primary cultures are not, however, generally suitable sources of angiogenic factor except for limited research purposes or small scale production. In order to provide a commercially significant source of angiogenic factor in terms of ready availability and adequate supply, production by cell culture of a suitable cell line is deemed necessary. As a practical matter, the cell line should not only have specific angiogenic factor activity, but it should also have good cell growth characteristics is terms of rapid growth and production of angiogenic factor on a sustained basis.

The term "cell line" is used herein in conformance with the well-known art accepted definition published by Federoff in the *Tissue Culture Association Manual,* Vol. 1, No. 1, pp. 53–57 (1975).

Further background information on angiogenic activity in normal tissues can be had by reference to a review by Ausprunk in Chapter 10 of "Handbook of Inflammation", Volume 1, at pages 321 and 343–346, Series ed. Glynn et al., Elsevier/North-Holland Biomedical Press, 1979.

DESCRIPTION OF THE INVENTION

The inventors have investigated numerous normal human cell lines for the production of angiogenic factor by cell culture but most of them have been eliminated as unsuitable candidates in view of their relatively poor angiogenic activity production or poor growth characteristics as above-defined.

Cell lines that have now unexpectedly been found by the inventors to have good growth characteristics in cell culture and to be able to elaborate the desired angiogenic factor in suitable quantities are the cell lines of human foreskin fibroblasts.

These cell lines are readily available to the public for cell culture research and other such purposes from cell culture repositories such as the American Type Culture Collection, Rockville, Md., and the Human Genetic Mutant Cell Repository of the Institute for Medical Research, Camden, N.J. Suitable such cell lines also can arise from subculturing of primary cell cultures which are started from tissues or cells obtained directly from surgical procedures. Illustrative examples of publically available human foreskin fibroblast cell lines are the cell lines available under the code designations AG1518, AG1519 and AG1523 from the Institute for Medical Research, Camden, N.J. and the cell line HR218 which is commercially available from HEM Research Inc., Rockville, Md.

In order to illustrate the invention, human foreskin fibroblast cell lines were initially maintained at 37° C. as monolayers in a series of 75 cm$^2$ T-flasks (Falcon Plastics) containing 50 ml Dulbecco's modification of Eagle's minimum essential medium (MEM) supplemented with 4.5 mg/ml glucose and 20% fetal bovine serum (KC Biologicals), without addition of any antibiotics. The flasks were charged with fresh medium every 1–2 days until confluency was reached in about 6–8 days.

It will be appreciated that other nutrient culture media for culture of the foreskin fibroblast cells can be used in place of Dulbecco's MEM, for example, any of the well-known tissue culture media described by H. J. Morton, *In Vitro* 6, 89–108 (1970). These conventional culture media contain known essential amino acids, mineral salts, vitamins and carbohydrates. They are also frequently fortified with mammalian sera such as fetal bovine serum. Suitable growth of the cells can be carried out at about 35°–38° C., but cell proliferation is best at 37° C. Growth under these cell conditions for about 4–8 days generally is sufficient to produce the desired angiogenic factor.

Currently, four different bioassays are used to detect the presence of angiogenic factor. They are:

(1) The chorioallantoic membrane (CAM) of the 10 to 11 day-old chick embryo; Auerback et al., *Devel. Biol.* 41, 391–94 (1974); Folkman, *Cancer Res.* 34, 2109–13 and 36, 110–114 (1976).

(2) The rat dorsal subcutaneous pouch; Folkman, *New Engl. J. Med.* 285, 1182–86 (1971); Phillips et al., *Int. J. Cancer* 17, 549–58 (1976).

(3) The rabbit cornea; Gimbrone et al., *J. Nat. Cancer Inst.* 50, 219–28 (1973); 52, 413–27 (1974).

(4) The hamster cheek pouch; Wolf, et al., *J. Invest. Dermatol* 61, 130–41 (1973).

The CAM assay was used herein for convenience in that many duplicate samples can be tested inexpensively. According to this test method, the CAM is exposed through a window in the shell of a 9-day-old chick egg. On day 11, the sample is implanted and read at 48–72 hours. Active material induces new vessels to grow in toward the implantation site, thereby producing a spoke wheel appearance. The reaction can be graded qualitatively and capillary proliferation continues up to day 17.

In addition to growth in T-flasks, the foreskin fibroblast cells can also be grown in conventional roller bottles. By this technique, cylindrical bottles are inoculated with cells and supplied with suitable nutrient medium and then rotated slowly about the long axis of the bottles by rollers or wheels on which they lie. The cells adhere evenly over the glass surface and eventually spread to form a monolayer covering it. They can be removed by scraping or by treatment with trypsin until the cells become loose. Roller tubes as described in U.S. Pat. No. 3,450,598, are similarly useful for practice of the present invention.

Alternatively, the cells can be grown to confluency on synthetic beads, microcarriers and other such support surfaces supplying a high surface area, for example, glass beads or rods, silica spherules, microspheres of organic polymeric materials such as DEAE-Sephadex, polyacrylonitrile, polyacrylamide, polystyrene latex particles, and on elongated hollow or solid fibers, and other such support surface means.

Other suitable, large-scale equipment and procedures for growing cells on attached solid support which can be adapted for culture of the foreskin, fibroblast cell lines will be readily apparent to the person skilled in the art by reference to well-known texts on cell culture and references cited therein such as, for example, Paul, "Cell and Tissue Culture," The Williams and Wilkins Company, Baltimore, Md., 4th ed. 1973, at pages 277–91; Kruse and Patterson, "Tissue Culture Methods and Apparatus", Academic Press, New York, 1973, at pages 283–392.

Various means can be used to recover fractions and concentrates of angiogenic factor from the cells and from cell product in the expended media following suitable growth of the cells. For example, the cells can be harvested and lysed by conventional means and angiogenic factor can then be recovered from the lysate by conventional techniques for the separation, isolation and purification of proteinaceous and other biological products in general. Suitable such procedures include, for example, dialysis, salt and solvent precipitation, ultracentrifugation, adsorption with gels, ion exchange chromatography with materials such as CM-cellulose, DEAE-cellulose, CM-Sephadex® and DEAE-Sephadex (Pharmacia AB) ion exchange resins, affinity chromatography, Sephadex gel filtration, electrophoresis such as agarose and polyacrylamide electrophoresis, SDS electrophoresis, isoelectric focusing and lyophilization. It will be appreciated that the inventors are not bound by any particular separation or isolation procedure or purity of the angiogenesis factor.

The following examples will further illustrate the invention although it shall be understood that the invention is not limited to these specific examples.

EXAMPLE 1

A sample of the HR218 foreskin fibroblast cell line was obtained from HEM Research Inc., Rockville, Md., at passage 19 (catalog #4-404). The cell line was maintained at 37° C. as a monolayer in a series of T-75 cm$^2$ tissue culture flasks (Falcon Plastics) containing 50 ml. Dulbecco's MEM supplemented with 4.5 mg/ml glucose and 20% fetal bovine serum (KC Biologicals) without addition of any antibiotics. The flasks were charged with fresh medium every 1–2 days. When confluency was reached after 6–8 days, the cells were subcultured 1:3 in the following manner:

The spent medium was poured off the monolayer and discarded. The monolayer then was rinsed twice with 10 ml phosphate buffered saline (PBS) with 0.02% ethylenediamine tetracetic acid (EDTA), at pH 7.4. The PBS was prepared by dissolving 80 grams NaCl, 2 grams KCl, 2 grams KH$_2$PO$_4$ and 21.6 grams Na$_2$HPO$_4$.7H$_2$O in 10 liters distilled water.

The cells were released from the surface of the flask by adding 5 ml. 0.05% trypsin in PBS with 0.02% EDTA and allowing the thus treated cells to stand 5 minutes at room temperature (ca. 22–25° C.). The suspension was divided equally into 3 fresh T-flasks containing 50 ml medium each.

To inoculate a roller bottle for cell culture in roller bottles, 3 of the confluent T-flasks were washed with PBS with EDTA and then trypsinized as above. Two-thirds of the suspension from these T-flasks were added to a CO$_2$ gassed roller bottle containing 100 ml. medium. The remainder of the suspension was added to three fresh T-flasks. Confluent roller bottles were split 1:3 by the same procedure as the T-flasks, except that 25–30 ml. PBS with EDTA were used for each rinse and 10 ml of the trypsin solution was used to suspend the cells.

CAM assays were carried out for obtaining an estimate of the angiogenic factor activity on the cell product after the cells had been thus subcultured in roller bottles through passage 24. In general, 6 to 10 eggs were used per assay and 200 μg (dry weight) of lyophilized sample material was dissolved and redried on a small plastic disk. The disk was placed sample side down onto the exposed CAM. The eggs were read for capillary proliferation toward the implantation site after 1 to 5 days following implantation and scored as active (positive, +) or inactive (negative, −), or as indefinite (neither positive nor negative, ±) relative to known control results. A known positive sample of tumor angiogenic factor (from Walker 256 Carcinosarcoma cells) was usually run as a positive control while, for comparison, sterile filtered bovine serum albumin (BSA) was always negative. The results of the assay were expressed as the number of positive eggs per total readable eggs. Eggs that were unreadable for various reasons, e.g. dried during the assay, or were ±, were omitted from the assay results stated below.

In this example, 27 roller bottles of confluent HR218 cells (750 cm² available surface/bottle) were harvested six days after the last subculture (passage 24) as follows:

Each bottle was washed twice with 25 ml PBS without EDTA. Twenty-five ml. of sterile water was then added to each bottle, and the cells were incubated for 30 minutes at 37° C. The cells were lysed by mechanical disruption. The lysate plus a 25 ml water rinse of each bottle was stored at −20° C. for further use or fractionation. Before freezing, a 35 ml. aliquot of the lysate was clarified by centrifugation (one 5-minute period at 5000×g, and then the supernatant for 30 minutes at 5000×g). The clarified lysate was concentrated in an Amicon B15 Minicon ® concentrator to a volume of about 50 μl. The concentrated lysate was evaporated on coverslips and tested for angiogenic factor activity in the CAM assay with the following results:

Concentrated lysate—5 positive out of 10 eggs
Control sample from Walker 256 Carcinosarcoma—7 positive out of 8 eggs
BSA control sample—0 positive out of 9 eggs The remaining lysate was unfrozen and clarified twice at 5000×g as above. The clarified lysate was concentrated to about 200 ml and dialyzed into low salt phosphate buffer (0.1 M $NaH_2PO_4$, 0.02% $NaN_3$, pH 6.1) in a Millipore Pellicon ® cassette concentration system. The concentrated lysate was added to 1.5 grams carboxymethyl (CM) Sephadex (particle size 40–120 μ, Sigma Chemical Co. catalog #C50–120) which had previously been swollen in low salt phosphate buffer. After stirring for 30 minutes at room temperature, the mixture was filtered and the filtrate was retained as the CM-I fraction. The CM-Sephadex gel was rinsed with low salt phosphate buffer and then poured into a glass column (2 cm. diameter). A high salt phosphate buffer (1 M NaCl, 0.1 M $NaH_2PO_4$, 0.02% $NaN_3$, pH 6.1) was applied to the column to release the protein from the CM-Sephadex. The column was set up so that the eluate flowed through a LKB Unicord II monitor (LKB Instruments, Inc.) set at 280 mm which recorded any protein eluted from the gel. The eluate was collected in fractions, with retention of that fraction (CM-II) which corresponded to the protein peak on the monitor.

Both the foregoing CM-I (173 mg. protein) and CM-II (5.8 mg. protein) fractions were dialyzed against distilled water and lyophilized. The lyophilized fractions were tested for angiogenic factor in the CAM assay as above with the following results:

CM-I—3 positive out of 7 eggs (or 3/7+)
CM-II—6 positive out of 6 eggs (or 6/6+)
Control sample from Walker 256 Carcinosarcoma cells—6 positive out of 8 eggs (or 6/8+)
BSA control sample—0 positive out of 6 eggs (or 0/6+)

EXAMPLE 2

A sample of the AG1518 human foreskin fibroblast cell line was obtained from the Institute for Medical Research, Camden, N.J. at passage 4. The cells were grown in T-flasks and roller bottles with 1:3 subculture in accordance with the procedure of Example 1. At the eighth passage, seven days since the last subculture, a single confluent roller bottle was rinsed twice with 25 ml volumes of PBS without EDTA and then incubated at 37° C. for 30 min. in 25 ml sterile distilled water. After mechanical disruption, the lysate plus 10 ml of distilled water rinse were combined, clarified by centrifugation as in Example 1, and concentrated in an Amicon B15 Minicon ® concentrator to a volume of about 50 μl. The concentrated lysate was tested for angiogenic factor activity in the CAM assay as described in Example 1. The assay results were as follows:

lysate 2/5+, Walker positive control 6/8+ BSA negative control 0/6+

EXAMPLE 3

The cell line AG1518 of Example 2 was grown to 27 roller bottles at passage 12. Nine days after the last subculture the cells were harvested and lysed according to the procedure of Example 1. A total 8.7 mg of DNA was detected in the lysate and the CM-I fraction had 113 mg of protein while the CM-II fraction had 8 mg of protein. This material was tested for angiogenic factor activity on two occasions. The results were as follows:

1st Test: CM-I 1/6+, CM-II 4/6+, control omitted
2nd Test: CM-I 1/6+, CM-II 5/7+, Walker positive Control 4/6+

EXAMPLE 4

The AG1518 cell line of Example 2 at passages 15 and 16 was grown to 209 roller bottles and harvested according to the procedure of Example 1 seven days after the last subculture. A total DNA concentration of 121 mg was detected in the lysate.

After concentration in the Millipore Pellicon ® concentrator, an aliquot was removed, dialyzed and lyophilized. This was an unfractionated sample. The CM-Sephadex fractions were isolated as in Example 1 with 1.2 gm of protein in the CM-I fraction and 90 mg of protein in the CM-II fraction. The material was tested for angiogenic factor activity in the CAM assay with results as follows:

Unfractionated sample 1/6+, CM-I 1/5+, CM-II 4/5+
Walker positive control ¾+, no negative control

EXAMPLE 5

A sample of a foreskin fibroblast cell line under the code designation MM was obtained from Dr. Thomas Merigan of Stanford University, Palo Alto, Calif. at passage 9. The cells were grown in T-flasks and roller bottles in accordance with the procedure of Example 1. At passage 13, after a growth time of 6 days, one roller bottle was harvested in accordance with the procedure of Example 3 and concentrated to about 50 μl in an Amicon B15 Minicon® concentrator. This concentrated lysate was tested for angiogenic factor activity in the CAM assay. The results were as follows:

Lysate ⅓+, controls omitted

EXAMPLE 6

The cell line MM described in Example 5 was grown to 21 roller bottles at passage 14 and harvested after 4 days according to the procedure of Example 1. A total of 19.1 mg of DNA was detected in the lysate and 103 mg of protein were found in the CM-I fraction and 5.8 mg of protein in the CM-II fraction. Several tests were run on the CAM to determine the angiogenic factor activity of these samples with results as follows:

Test 1 CM-I 3/3+, CM-II ⅔+, Walker Positive Control 3/3+

Test 2 CM-I 0/6+, CM-II 4/5+, Walker Positive Control 4/6+

Test 3 - - - CM-II 3/3+, Walkter Positive Control 5/5+

Test 4 CM-I 1/5+, - - - Walker Positive Control 3/3+

EXAMPLE 7

A sample of the AG1523 human foreskin fibroblast cell line was obtained from the Institute for Medical Research, Camden, N.J. at passage 3. The cells were grown in T-flasks and roller bottles in accordance with the procedure of Example 1. At passage 9, thirty roller bottles were harvested as in Example 1, six days after the last subculture. An unfractionated (35 ml) sample was reserved from this lysate and concentrated in an Amicon Minicon® concentrator to about 50 µl as in Example 1. A total of 23.6 mg of DNA was detected in the lysate and the CM-I fraction had 168 mg of protein, the CM-II fraction 7.14 mg protein. Tests were made on this material in the CAM assay to determine angiogenic factor activity with results as follows:

Test 1: CM-I 4/7+, CM-II 2/6+, Walker Positive Control 2/7+

Test 2: Unfractionated sample 0/5+, Walker Positive Control 4/8+

Test 3: CM-I ½+, CM-II 4/5+, Walker Positive Control 4/5+

EXAMPLE 8

A sample of the AG1519 human foreskin fibroblast cell line was obtained from the Institute for Medical Research, Camden, N.J. at passage 3. The cells were grown in T-flasks and roller bottles in accordance with the procedure of Example 1. At passages 11, 12 and 13, six days after the last subculture, twenty-eight roller bottles were harvested according to the procedure of Example 1. An unfractionated 35 ml aliquot was removed and concentrated in an Amicon Minicon® concentrator to about 50 µl as in Example 1. The total DNA detected in the lysate was 19.3 mg. The CM-I protein was 138 mg and the CM-II was 6.7 mg. CAM assays were used to determine angiogenic factor activity with results as follows:

Test 1: Unfractionated sample 6/6+, Walker Positive Control 6/6+

Test 2: CM-I 1/7+, CM-II 5/7+, Walker Positive Control 2/7+

The CM-Sephadex used in the foregoing examples is a well-known cross-linked dextran material having carboxymethyl functional groups and serves as a weakly acidic cation exchanger. Its use for obtaining an active fraction of tumor angiogenic factor from tumor cells is described by Tuan et al, *Biochemistry* 12 (17), 3159–65 (1973).

Various other examples of the invention will be apparent to the person skilled in the art after reading the present disclosure without departing from the spirit and scope of the invention. It is intended that all such other examples be included within the scope of the invention.

What is claimed is:

1. Process for the production of human angiogenic factor in vitro comprising growing cells of human foreskin fibroblast cell line on support surface in nutrient culture medium at about 35°–38° C. for a sufficient time to elaborate angiogenic factor and isolating the resulting angiogenic factor from the cells or cell product.

2. The process of claim 1 in which the nutrient culture medium is Dulbecco's modification of Eagle's minimum essential medium.

3. The process of claim 1 in which the nutrient culture medium is fortified with mammalian serum.

4. The process of claim 1 in which the angiogenic factor is isolated by extraction from the cells.

5. The process of claim 1 in which the nutrient culture medium is Dulbecco's modification of Eagle's minimum essential medium and is fortified with fetal bovine serum and in which the angiogenic factor is isolated by extraction from the cells and concentration by carboxymethyl Sephadex chromatography.

* * * * *